(12) United States Patent
Huang et al.

(10) Patent No.: US 8,076,511 B2
(45) Date of Patent: Dec. 13, 2011

(54) PREPARATIVE-SCALE SEPARATION OF ENANTIOMERS OF CHIRAL CARBOXYLIC ACIDS

(75) Inventors: Der-Shing Huang, Folsom, CA (US); Olivier Dapremont, Citrus Heights, CA (US); Patrick Berget, Sacramento, CA (US); Xa Her, Rancho Cordova, CA (US); Darin Sanchez, Folsom, CA (US)

(73) Assignee: Ampac Fine Chemicals LLC., Rancho Cordova, CA (US)

( * ) Notice: Subject to any disclaimer, the term of this patent is extended or adjusted under 35 U.S.C. 154(b) by 837 days.

(21) Appl. No.: 11/750,502

(22) Filed: May 18, 2007

(65) Prior Publication Data

US 2008/0287704 A1    Nov. 20, 2008

(51) Int. Cl.
*C07C 51/42* (2006.01)
(52) U.S. Cl. ........ 562/580; 562/401; 562/402; 562/400; 562/405; 562/579
(58) Field of Classification Search .......................... None
See application file for complete search history.

(56) References Cited

U.S. PATENT DOCUMENTS 5,484,530 A   1/1996 Pirkle et al.
6,333,426 B1 * 12/2001 Moller et al. ................... 560/25

FOREIGN PATENT DOCUMENTS

WO    WO 2006/011047 A1   2/2006
WO    WO 2006011047 A1 *  2/2006

OTHER PUBLICATIONS

Cia, Xiaojun et al.; "Enantioseparation of acidic compounds on chiral stationary phase by high performance liquid chromatography"; 2004, *Fenxi Huaxue*, vol. 32, No. 2, pp. 134-138.
Miller, Larry et al.; "Chromatographic resolution of the enantiomers of a pharmaceutical intermediate from the milligram to the kilogram scale"; 1999, *Journal of Chromatography*, vol. 849, pp. 309-317.
Xiaojun, Cai et al.; "Enahtioseparation of acidic compounds in chiral stationary phase by high performance liquid chromatography"; 2004, *Chinese Journal of Analytical Chemistry*, vol. 32, No. 2, pp. 134-138.

* cited by examiner

*Primary Examiner* — Sudhakar Katakam
(74) *Attorney, Agent, or Firm* — Kilpatrick Townsend & Stockton LLP.; M. Henry Heines

(57) ABSTRACT

High yields and purity are obtained in the purification of enantiomers of chiral carboxylic acids by preparative-scale chromatography by including a tertiary alcohol in the mobile phase in conjunction with an acidic modifier and a hydrophobic solvent. The tertiary alcohol is superior to other, more commonly used alcohols by reducing the extent of esterification of the enantiomer that otherwise lowers the yield and the purity.

16 Claims, No Drawings

PREPARATIVE-SCALE SEPARATION OF ENANTIOMERS OF CHIRAL CARBOXYLIC ACIDS

BACKGROUND OF THE INVENTION

1. Field of the Invention

This invention resides in the field of chiral separations, procedures for performing such separations, and the materials used in the procedures. The separations addressed by this invention are those of chiral drugs, particularly chiral carboxylic acids, in which one enantiomer is superior to the other in therapeutic effect.

2. Description of the Prior Art

Many chiral drugs, particularly homochiral drugs, are known to have enantiomers that perform differently in terms of pharmacological activity, toxicological considerations, or both. One class of chiral drugs that benefit from enantioselectivity are chiral carboxylic acids, notably 2-aryl carboxylic acids. Included among these are flurbiprofen (2-(2-fluoro-4-biphenylyl)-propionic acid), ibuprofen, (2-(4-isobutylphenyl)-propionic acid), naproxen (2-(6'-methoxy-2'-naphthyl) propionic acid), ketoprofen (2-(3-benzoylphenyl)propionic acid), carprofen (6 chloro-α-methyl-9H-carbazole-2-acetic acid), furaprofen (α-methyl-3-phenyl-7-benzofuranacetic acid), cicloprofen (α-methyl-9H-fluorene-2-acetic acid), cliprofen (3-chloro-α-methyl-4-(2-thienylcarbonylbenzene) acetic acid), indoprofen (4-(1,3-dihydro-1-oxo-2H-isoindol-2-yl)benzene acetic acid), pirprofen (3-chloro-4-(2,5-dihydro-1H-pyrrol-1-yl)benzeneacetic acid), and surprofen (α-methyl-4-(2-thienylcarbonyl)benzeneacetic acid). Disclosures of the benefits of enantioselectivity for these drugs and of methods of achieving their enantioselectivity are found in Zambon Group S.p.A. European Patent Application No. EP 0 719 755 A1, published Jul. 3, 1996, and its counterpart, Pozzoli, C., et al., U.S. Pat. No. 5,840,964, issued Nov. 24, 1998; Hardy, R., et al., International Patent Application Publication No. WO 94/12460, publication date Jun. 9, 1994, and its counterpart, Hardy, R., et al., U.S. Pat. No. 5,599,969, issued Feb. 4, 1997; Sunshine, A., et al., U.S. Pat. No. 5,286,751, issued Feb. 15, 1994; and Iredale, J., et al., "The Effects of pH and Alcoholic Organic Modifiers on the Direct Separation of Some Acidic, Basic and Neutral Compounds on a Commercially Available Ovomucoid Column," *Chromatographia* 31 (7/8), 329-334 (1991).

For any chiral drug of which one enantiomer is therapeutically superior to the other, administration of the desired enantiomer in isolated form will give the drug its maximal effect, and a number of analytical and preparative procedures have been developed for this purpose. These include manufacturing procedures, such as asymmetric synthesis and biocatalysis, that produce the desired enantiomer directly. The alternative to enantioselective manufacturing is the isolation or purification of the desired enantiomer from a racemic mixture. Purification techniques that have been developed for this purpose include crystallization, chemical resolution, the use of chiral membranes, and chiral chromatography. Chiral chromatography has the potential of being the most efficient since it does not involve the specialized synthesis steps involved in asymmetric synthesis or the additional processing steps involved in chemical resolution such as salt formation and product recovery from the salt. Nor is chiral chromatography plagued by the low yields that are typical of both crystallization techniques and techniques involving chiral membranes. The appeal of chiral chromatography has led to the development of a variety of chiral chromatographic techniques based on liquid, gas, subcritical fluid, and supercritical fluid chromatography, and a variety of chiral stationary phases.

One means of achieving peak separation in chiral chromatography is the use of a solvent mixture containing a non-polar solvent such as hexane or heptane and one or more alcoholic compounds. The retention of enantiomers is dependent on the polarity of the mobile phase and hence the separation can be tuned by variation of the ratio of alcohol to non-polar solvent. This use of alcohols is disclosed in Iqbal, R., et al., "Chiral separations in microemulsion electrokinetic chromatography—Use of micelle polymers and microemulsion polymers," *J. Chromatog. A* 1043 (2004) 291-302. This paper reports the use of 1-butanol and n-heptane in combination with a microemulsion of polysodium N-undecenoyl-D-valinate in a capillary electrophoresis column. Another disclosure of the use of alcohols is Wang, T., et al., "Effects of alcohol mobile-phase modifiers on the structure and chiral selectivity of amylase tris(3,5-dimethylphenylcarbamate) chiral stationary phase," *J. Chromatog. A* 1015 (2003) 99-110. In this paper, Wang et al. report the use of isopropanol, t-butyl alcohol, and ethanol in high-performance liquid chromatography (HPLC). Still another disclosure is found in Iredale, J., et al. (1991), cited above, which reports the use of various $C_1$-$C_4$ alcohols as mobile phase modifiers in an HPLC column in which the stationary phase is an ovomucoid protein on a silica support.

In traditional chromatography, the problems of peak separation are often addressed by increasing the path length of the solutes through the separation medium. This can be impractical, however, since it may require excessive column lengths and the high back pressures that typically occur with long columns. One class of chromatographic methods that improves performance for difficult separations is Multi-Column Continuous Chromatography (MCC), of which one mode of operation is Simulated Moving Bed (SMB) chromatography. SMB has achieved wide recognition for chiral separations. In SMB, the mobile phase flows in counter-current manner against the "stationary" phase (solid media), allowing the mixture to be separated to flow in a continuous flow, thereby potentially increasing the throughput of the process. To achieve this in practical application, a series of packed-bed columns are arranged in series in a ring formation that is divided into sections, typically four such sections for SMB, with one or more columns per section. Only the mobile phase and the points of inlet and outlet around the ring are moved while the beds themselves remain stationary. Two fluid inlets (one for feed and the other for eluent) and two fluid outlets (one for extract and the other for raffinate) are distributed around the ring of columns such that the inlets alternate with the outlets. The mobile phase moves in one direction around the ring, while at regular intervals of time the inlets and outlets are switched, traveling around the circle in the same direction as the mobile phase flow. Each port thus alternates between serving as an inlet and as an outlet, and between the two types of inlet as well as the two types of outlet. Descriptions of SMB chromatography and its use in separating enantiomers are found in Miller, L., et al., "Chromatographic resolution of the enantiomers of a pharmaceutical intermediate from the milligram to the kilogram scale," *J. Chromatog. A*, 849, no. 2, 309-317 (1999); Negawa, M., et al., U.S. Pat. No. 5,434,298 (issued Jul. 18, 1995); Nagamatsu, S., et al., U.S. Pat. No. 6,217,774 (issued Apr. 17, 2004); Ikeda, H., et al., U.S. Pat. No. 6,533,936 (issued Mar. 18, 2003); Ohnishi, A., et al., United States Patent Application Publication No. US 2005/0054878 A1, published Mar. 10, 2005; and *Chiral*

*Separation Techniques—A Practical Approach*, 3d ed., Subramanian, G., ed., Wiley-VCH Verlag GmbH & Co. KGaA, Wernheim, Germany (2007).

When separating acidic or basic racemates, the inclusion of an organic acid or organic base modifier in the mobile phase is recommended to improve the separation by achieving a better peak shape. Carboxylic acids such as acetic acid, trifluoroacetic acid, and formic acid have been used for this purpose in separations of chiral carboxylic acids. A disclosure of the use of this type of modifier is found in *Chiral Separation Techniques—A Practical Approach*, 3d ed., Subramanian, G., ed., Wiley-VCH Verlag GmbH & Co. KGaA, Wernheim, Germany (2007). The combination of an acidic modifier with an alcohol thus produces a system that will provide optimal conditions for the separation. Unfortunately, at production-scale separations where the system components remain in contact for extended periods of time, the alcohols and the acid will combine to form an ester, reducing the yield and the final purity of the product.

SUMMARY OF THE INVENTION

It has now been discovered that the advantages of the use of alcohols and organic acids as modifiers in the chromatographic separation of enantiomers of chiral carboxylic acids can be achieved while still obtaining a product in high yield and high purity, even in preparative-scale separations, by using a sterically hindered alcohol as the alcoholic component of the mobile phase. To prepare the feed for the separation, therefore, the racemic mixture is dissolved in a solution of the sterically hindered alcohol and the organic acid in a hydrocarbon solvent. The resulting solution containing the racemic mixture is then separated by chromatography, either in a batch or a continuous-flow separation mode, into an extract and a raffinate. The extract and raffinate are collected and the one that contains the enantiomer of interest is concentrated by conventional evaporation techniques. A key discovery in accordance with this invention is that the selected enantiomer undergoes little or no esterification during storage in solution in the mobile phase prior to final isolation, even if storage continues for an extended period of time. The desired product retains its purity level, relative to esterification, through the isolation stage by evaporation despite the conditions required for this operation. Both enantiomers can be purified and concentrated in this manner and will retain their purity levels or at least suffer only a minimal loss of purity. This beneficial use of a sterically hindered alcohol applies to any chromatographic separation process of a chiral carboxylic acid in which an alcoholic modifier is included for improving the separation.

DETAILED DESCRIPTION OF THE INVENTION AND PREFERRED EMBODIMENTS

Sterically hindered alcohols for use in the practice of this invention are tertiary alcohols, i.e., those in which the carbon atom to which the hydroxyl group is bonded is fully substituted, that will be miscible with the mobile phase vehicle. Any common substituents can be included, provided that they are inert to the enantiomers being separated and to the other components of the feed mixture. Preferred substituents are alkyl groups, particularly saturated alkyl groups of 1-3 carbon atoms each. The most preferred tertiary alcohols are those of four to six carbon atoms in the molecule as a whole. Examples of tertiary alcohols that can be used in the practice of this invention are t-butanol, 2-methyl-2-butanol, 3-methyl-3-pentanol, and 2,3-dimethyl-2-butanol. The most preferred is t-butanol.

Preferred mobile phase vehicles are hydrophobic solvents, most preferably alkanes, whether linear, branched, or cyclic, that are liquid at ambient temperature and have boiling points between 50° C. and 150° C. Particularly preferred examples are n-hexane and n-heptane, with n-heptane the most preferred. The proportion of the alcohol to the hydrocarbon solvent is preferably within the range of from about 1:10 to about 1:1 by volume.

Any organic acid that will improve the separation by reduction of the peak broadening and is chemically inert relative to the enantiomers and the other components of the feed mixture can be used. The organic acid can be substituted or unsubstituted and is preferably one that has a maximum of four carbon atoms. Examples of suitable organic acids are acetic acid, formic acid, and trifluoroacetic acid. Acetic acid is particularly preferred. The concentration of the acid in the mixture of the alcohol and the hydrophobic solvent can vary and is not critical to the success of the invention. In most cases, best results will be obtained with an acid concentration within the range of from about 0.03% to about 1.0% by weight, most preferably from about 0.05% to about 0.5% by weight.

For the chromatographic separation, a wide variety of chiral stationary phases can be used. The most common stationary phases used for preparative separations are polysaccharide derivatives such as esters and carbamates of cellulose or of amylose, on an inert solid support. Nano-structure nylon-like biopolymers can also be used. Specific examples are cellulose triacetate (CHIRALCEL® CTA, CHIRALCEL OA), cellulose tribenzoate (CHIRALCEL OB, CHIRALCEL OB-H), cellulose tri-4-methylbenzoate (CHIRALCEL OJ, CHIRALCEL OJ-R), cellulose tricinnamate (CHIRALCEL OK), cellulose tri-3-methylbenzoate (CMB), cellulose triphenylcarbamate (CHIRALCEL OC), cellulose tri-3,5-dimethylphenylcarbamate (CHIRALCEL OD, CHIRALCEL OD-H, CHIRALCEL OD-R, CHIRALCEL OD-RH), cellulose 4-chlorophenylcarbamate (CHIRALCEL OF), cellulose tri-4-methylphenylcarbamate (CHIRALCEL OG), amylose tris-3,5-dimethylphenylcarbamate (CHIRALPAK® AD, CHIRALPAK AD-R, CHIRALPAK AD-RH), amylose tris-(S)-α-methylphenylcarbamate (CHIRALPAK AS), and amylose tris-(R)-α-methylphenylcarbamate (CHIRALPAK AR). These and various other chiral stationary phases are available from Chiral TEchnologies, Inc., West Chester, Pa., USA; Advanced Separation Technologies Inc., Whippany, N.J., USA; Eka Chemicals Ab, Bohus, Sweden; Rockland Technologies, Inc., Newport, Del., USA; Merck KGaA, Darmstadt, Germany; Regis Technologies, Inc., Morton Grove, Ill., USA; and Evolved Nanomaterial Sciences, Inc., Cambridge, Mass., USA. The chiral stationary phases in general are supported on a solid support which is typically silica gel or a macroporous silica. The product CHIRALPAK AD, for example, is amylose tris(3,5-dimethylphenylcarbamate) on a macroporous silica support. Chiral stationary phases typically consist of particles whose size ranges from about 5 microns to about 300 microns, preferably from about 10 microns to about 50 microns.

Of the chromatographic procedures to which this invention extends, a preferred group are the procedures generically known as Multi-Column Continuous Chromatography (MCC). Any of various forms of MCC can be used, and each form can be performed under a variety of operating conditions, including the composition of the stationary phase, the composition of the eluent or mobile phase, the number and sizes of the columns, the rate and protocol of column switching (synchronous or asynchronous), the feed rate of the feed mixture containing the enantiomers, the feed rate of the eluent, and the number of points of introduction into the system for both the feed and the eluent. One form of MCC chromatography that can be used is conventional SMB chromatography, in which the columns are typically arranged in four zones, the zones separated by injection points and removal points and connected in series to form a ring, each zone consisting of one or more columns. By valve switching, the injection and removal points are advanced around the ring of columns so that each zone serves in succession as an adsorption zone, an eluent recovery zone, a desorption zone, and a concentration zone, with the feed entering the circuit immediately upstream of the adsorption zone and the eluent entering immediately upstream of the desorption zone, the raffinate withdrawn between the adsorption and eluent recovery zones, and the extract withdrawn between the desorption and concentration zones. A diagrammatic depiction of this arrangement is found in Ohnishi et al., U.S. Patent Application Publication No. US 2005/0054878, published Mar. 10, 2005.

A variation on the conventional SMB system is the variable column system (commonly referred to as "Varicol") in which the shifts in the inlet and outlet ports are performed in a non-synchronous manner. This is achieved by including one or more ports in addition to those that are in use at any one point in time, and shifting the feed inlet, for example, by itself from one port to an adjacent downstream port, and then shifting the eluent inlet and the extract and raffinate outlets together after an interval. The switching interval is thus divided in half, with the feed inlet shifted after the first half and the eluent inlet and extract and raffinate outlets at the end of the second half. A further variation is the use of multiple distributed feeds, in which the total number of ports is five or more, and the feed is introduced at two adjacent, but spaced-apart, ports. Switching can be performed according to various protocols, including those in which the feed enters through two ports at all times and those in which the number of ports used for feed, or the choice of feed port, varies with the point in time in the switching cycle. A still further variation is one in which a solvent gradient, i.e., a gradient in solvent concentration, is imposed on the mobile phase to provide enhanced control of solubility and consequently of adsorption and desorption. A solvent gradient is achieved by using one concentration as the carrier vehicle for the feed and another as the eluent, or by introducing the eluent at multiple points each with a different concentration. A still further variation is the Improved Simulated Moving Bed (ISMB) system in which the successive feed/extraction stages (i.e., the introduction of feed and eluent with the simultaneous withdrawal of extract and raffinate) are separated by a recycle step in which no introductions or withdrawals are made. Other variations known in the art can be used as well.

In SMB systems in general, the length of each column can vary, although best results will be obtained with columns ranging in length from about 5 cm to about 50 cm, preferably from about 8 cm to about 12 cm. Column widths will typically range from about 4.6 mm to about 1,000 mm. The feed rates of the starting enantiomer mixture and of the eluent can likewise vary, and the optimal rates will be readily determinable by routine experimentation. In SMB units equipped with four columns each of which is 4.6 mm diameter, the feed rate of eluent will range from about 0.1 mL/min to about 20 mL/min, and preferably from about 2 mL/min to about 6 mL/min. In references herein to chromatographic separations in general, the term "extract" refers to the stream containing the enantiomer that is preferentially adsorbed by the solid phase after that enantiomer has been desorbed from the solid phase by the eluent, while the term "raffinate" refers to the stream containing the enantiomer that preferentially remains in the mobile phase. The materials, conditions, and procedures used in the chromatographic separation will be such that the extract contains one enantiomer to the substantial exclusion of the other, and the raffinate contains the other enantiomer to the substantial exclusion of the first. The term "substantial exclusion" is used herein to denote an amount that is small enough to have at most a negligible or insignificant effect on the therapeutic or toxicological activity, whether the activity be positive or negative, of the enantiomer that is present in a significant amount. In preferred cases, "substantial exclusion" means less than 10%, more preferably less than 5%, and most preferably less than 1%, in terms of total enantiomer content, i.e., excluding solvents and modifiers.

As a preparative separation procedure, the desired product of the process of this invention can be the extract, the raffinate, or both, achieved either as a batch process or a continuous process. Batch processes will typically be performed with a starting solution that is 100 mL or more in volume, preferably 200 mL or more, and most typically from about 10 L to about 100 L in volume. In general, batch processes can handle feed volumes as large as 2,000 gallons. The separation process will typically be performed with a starting solution of the racemate dissolved in the mobile phase at a volume that is sufficient to allow for 1 to 400 hours of operations, preferably 24 to 48 hours. Following the separation, the product will typically be concentrated and stored until ready for use or for shipping. As noted above, it is during these stages that the purity and yield tend to drop due to esterification and in which the present invention demonstrates its greatest advantages. Concentration of the enantiomer(s) from either the extract, the raffinate, or both is achieved by conventional means, preferably by evaporation of the hydrocarbon serving as the vehicle in the eluent. Evaporation can be performed by natural circulation evaporators, forced-circulation evaporators, or film-type evaporators, and examples of film-type evaporators are falling-film evaporators and agitated-film evaporators. Depending on the solvents present, evaporation can occur as low as 20° C. or above. Flash evaporation, including multi-stage flash evaporation, can also be used. Steam and other conventional heat transfer media can be used to supply heat to the evaporator. Evaporation will typically be performed at an elevated temperature, preferably 40° C. or above, and often at a subatmospheric pressure, preferably 80 to 150 mbar. Storage of the concentrated solution will then typically occur for at least one hour, and in many cases, for at least ten hours, or at least 24 hours, or for several days or more.

As noted above, this invention is applicable to chiral carboxylic acids, and particularly to 2-arylpropionic acids, examples of which are listed above. Preferred among the 2-arylcarboxylic acids are flurbiprofen, ibuprofen, and naproxen, with flurbiprofen being of particular interest. In the case of flurbiprofen, both the R-enantiomer and the S-enantiomer have specific therapeutic activities that are different for each enantiomer, and the SMB separation procedure allow for recovery of both enantiomers at high chiral purity.

The following example is offered for purposes of illustration only.

EXAMPLE

A feed solution containing a racemic mixture of flurbiprofen was prepared by dissolving the racemic mixture in a mobile phase mixture consisting of 85% heptane (technical grade) and 15% t-butyl alcohol (HPLC grade) and 0.1% acetic acid (all by volume) to achieve a flurbiprofen concentration of 34.2 g/L for a total feed mixture volume of 3.1 L. The feed solution was fed into a simulated moving bed (SMB) unit equipped with eight columns in four groups of two columns each, each column having an internal diameter of 4.6 mm and a length of 10 cm and packed with CHIRALPAK™ AD (20 µm). The mobile phase mixture identified above was used as the eluent in the SMB unit, the flow rates 3.39 mL/min of eluent, 0.15 mL/min of feed, and the withdrawal rates were 0.46 mL/min of extract (R-flurbiprofen) and 1.25 mL/min of raffinate (L-flurbiprofen). The zone I flow rate, i.e., the flow rate in the zone between the removal of the extract and the introduction of the eluent, was 5.2 mL/min. The unit was operated with a column switching period of 0.8 min, and at a temperature of 25° C. Both the extract and the raffinate were concentrated by evaporation on rotary evaporators at a pressure of 100 mbar and a temperature of 40° C. After allowing the extract and raffinate to stand for at least 24 hours, the extract and raffinate were then separately analyzed for purity by HPLC. The analysis determined that the enantiomeric purity of the R-enantiomer in the extract was 99%, and the enantiomeric purity of the S-enantiomer in the raffinate was 98%.

In the claims that follow, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

While the foregoing description describes various alternatives to the components shown in the Figures, still further alternatives will be apparent to those who are skilled in the art and are within the scope of the invention.

What is claimed is:

1. A process for recovering a selected enantiomer from a mixture of first and second enantiomers of a chiral carboxylic acid selected from the group consisting of flurbiprofen, ibuprofen, and naproxen, said method comprising:
    (a) preparing a feed solution of solutes dissolved in a hydrophobic alkane having a boiling point between 50° C. and 150° C., said solutes comprising said first and second enantiomers, an organic acid selected from the group consisting of $C_1$-$C_4$ alkyl carboxylic acids and halogen-substituted $C_1$-$C_4$ alkyl carboxylic acids, and a tertiary alcohol;
    (b) passing said feed solution through a chromatographic separation system to achieve an extract and a raffinate as separate product solutions, said raffinate having dissolved therein said first enantiomer to the substantial exclusion of said second enantiomer, and said extract having dissolved therein said second enantiomer to the substantial exclusion of said first enantiomer; and
    (c) collecting said product solution containing said selected enantiomer, concentrating said collected product solution by evaporation of said hydrocarbon solvent to form a concentrated product, and storing said concentrated product for at least one hour.

2. The process of claim 1 wherein said chromatographic separation system is a simulated moving bed chromatography system with synchronous shifting of inlet and outlet ports.

3. The process of claim 1 wherein said chromatographic separation system is a simulated moving bed chromatography system with non-synchronous shifting of inlet and outlet ports.

4. The process of claim 1 wherein said chiral carboxylic acid is flurbiprofen.

5. The process of claim 1 wherein said organic acid is a member selected from the group consisting of acetic acid, trifluoroacetic acid, and formic acid.

6. The process of claim 1 wherein said organic acid is acetic acid.

7. The process of claim 1 wherein said tertiary alcohol is a member selected from the group consisting of t-butanol, 2-methyl-2-butanol, 3-methyl-3-pentanol, and 2,3-dimethyl-2-butanol.

8. The process of claim 1 wherein said tertiary alcohol is t-butanol.

9. The process of claim 1 wherein said hydrocarbon solvent is a member selected from the group consisting of n-heptane and n-hexane.

10. The process of claim 1 wherein said chiral carboxylic acid is flurbiprofen, said organic acid is acetic acid, and said tertiary alcohol is t-butanol.

11. The process of claim 1 wherein said separation system is a simulated moving bed chromatography system utilizing a stationary phase comprising an amylose derivative on a solid support.

12. The process of claim 11 wherein said amylose derivative is amylose tris(3,5-dimethylphenylcarbamate) and said solid support is macroporous silica.

13. The process of claim 1 comprising concentrating said collected product solution in step (c) by evaporation of said hydrocarbon solvent at a temperature in excess of 20° C.

14. The process of claim 1 comprising concentrating said collected product solution in step (c) by evaporation of said hydrocarbon solvent at a temperature in excess of 40° C.

15. The process of claim 1 wherein step (c) comprises storing said concentrated product for at least ten hours.

16. The process of claim 1 wherein step (c) comprises storing said concentrated product for at least 24 hours.

* * * * *